United States Patent [19]
Nakamura et al.

[11] Patent Number: 5,853,711
[45] Date of Patent: Dec. 29, 1998

[54] WATER-IN-OIL EMULSION COSMETIC COMPOSITION

[75] Inventors: Tadashi Nakamura; Kenzo Ito, both of Yokohama, Japan

[73] Assignee: Shiseido Company, Ltd, Tokyo, Japan

[21] Appl. No.: 723,937

[22] Filed: Sep. 26, 1996

[30]     Foreign Application Priority Data

Sep. 29, 1995  [JP]  Japan .................................... 7-277121
Sep. 29, 1995  [JP]  Japan .................................... 7-277122
Sep. 29, 1995  [JP]  Japan .................................... 7-277123

[51] Int. Cl.$^6$ ................................ A61K 7/02; A61K 7/48
[52] U.S. Cl. ......................... 424/78.03; 424/401; 424/69; 514/63; 514/844; 514/845; 514/846; 514/847; 514/937
[58] Field of Search .................. 424/401, 78.03, 424/69; 514/63, 844–847, 937

[56]          References Cited

FOREIGN PATENT DOCUMENTS

| | | |
|---|---|---|
| 293795 | 12/1988 | European Pat. Off. . |
| 295886 | 12/1988 | European Pat. Off. . |
| 381166 | 8/1990 | European Pat. Off. . |
| 686391 | 12/1995 | European Pat. Off. . |
| 61-129033 | 6/1986 | Japan . |
| 1-175917 | 7/1989 | Japan . |
| 2-258711 | 10/1990 | Japan . |
| 3-72942 | 3/1991 | Japan . |
| 4-17162 | 3/1992 | Japan . |
| 4-66446 | 10/1992 | Japan . |

OTHER PUBLICATIONS

Abstract of JPA–61–129033, Water in Oil Emuslifier Composition, 92 C 381.
Abstract of JPA–2–243612, Cosmetic, 128 C 788.
Abstract of JPA–61–194009, Makeup Cosmetic, 74 C 398.
Abstract of JPA–63–313710, Face Cleaning Cosmetic, 166 C 585.
Derwent Database, section Ch, Week 9616, AN 96–156965, abstract of JP 08–040 831 (1996).

*Primary Examiner*—Jyothsna Venkat
*Attorney, Agent, or Firm*—Sprung Kramer Schaefer & Briscoe

[57]          ABSTRACT

A water-in-oil type emulsion cosmetic composition comprising a mixed powder of (A) an organopolysiloxane elastomer spherical powder having an average particle size of 2.0 to 5.0 $\mu$m and a particle size distribution of 1 to 15 $\mu$m and (B) a hydrophobic silica powder having an average particle size of not more than 0.2 $\mu$m, wherein the weight ratio of (A) to (B) is 1:0.1 to 1:5, (C) an oil phase or (C') an oil phase containing at least 30% by weight, based upon the total oil phase component, of silicone oil, (D) an emulsifying agent having an HLB value of not more than 7, and (E) water, and, optionally, (F) a metallic soap or (G) an organically modified clay mineral.

14 Claims, No Drawings

WATER-IN-OIL EMULSION COSMETIC COMPOSITION

BACKGROUND OF THE INVENTION

1. Field of the Invention

The present invention relates to a water-in-oil type (i.e., "W/O" type) emulsion cosmetic composition (or a cosmetic composition in the form of a W/O type emulsion). More specifically, the present invention relates to a water-in-oil type emulsion cosmetic composition which does not increase the viscosity of the outer phase, which exhibits an excellent emulsion state, is free from changes due to temperature or the elapse of time, and further has a good spreadability (or slip) on the skin when applied thereto and has a fresh, excellent feeling in use.

2. Description of the Related Art

In the past, water-in-oil type emulsion (or emulsified) cosmetic compositions having a high stability have been obtained by increasing the viscosity of the outer phase (i.e., oil phase) and mixing in solid and semisolid oil components. Thus, an oily and sticky feeling in use is resulted and the evaluation result as a cosmetic was low. However, emulsions containing relatively large amounts of an aqueous phase have been developed and the solid and semisolid oil components in the oil phase can be greatly reduced, as shown in, for example, the "water-in-oil type emulsifying agent composition" of Japanese Unexamined Patent Publication (Kokai) No. 53-21393 and the "water-in-oil type emulsion composition" of Japanese Unexamined Patent Publication (Kokai) No. 61-129033. However, even emulsion cosmetic compositions containing these emulsion compositions provided the high stability by increasing the viscosity of the outer phase in a similar manner, and therefore, the spreadability (or slip) at the time of application to the skin was poor and there was an insufficient feeling of freshness. Therefore, development has been desired of a water-in-oil type emulsion cosmetic composition having excellent stability, a good spreadability (or slip), and a freshness and good feeling in use even with a low viscosity of the outer phase.

SUMMARY OF THE INVENTION

Accordingly, the objects of the present invention are to eliminate the above-mentioned problems in the prior art and to provide a water-in-oil type emulsion cosmetic composition having a good spreadability, a fresh feeling in use, and good stability.

Other objects and advantages of the present invention will be apparent from the following description.

In accordance with the first aspect of the present invention, there is provided a water-in-oil type emulsion cosmetic composition comprising a mixed powder of (A) an organopolysiloxane elastomer spherical powder having an average particle size of 2.0 to 5.0 $\mu$m and a particle size distribution of 1 to 15 $\mu$m and (B) a hydrophobic silica powder having an average particle size of not more than 0.2 $\mu$m, wherein the weight ratio of (A) to (B) is 1:0.1 to 1:5, (C) an oil phase, (D) an emulsifying agent having an HLB value of not more than 7 and (E) water. The weight ratio of the mixed powder of (A)+(B) to the oil phase (C) is preferably 1:5 to 1:30 and the content of (A)+(B)+(C) is preferably 9.0 to 90.0% by weight, the content of the emulsifying agent having an HLB value of not more than 7 (D) is preferably 0.01 to 5.0% by weight, and the content of the water (E) is preferably 9.0 to 90.0% by weight.

In accordance with the second aspect of the present invention, there is also provided a water-in-oil type emulsion cosmetic composition comprising a mixed powder of (A) an organopolysiloxane elastomer spherical powder having an average particle size of 2.0 to 5.0 $\mu$m and a particle size distribution of 1 to 15 $\mu$m and (B) a hydrophobic silica powder having an average particle size of not more than 0.2 $\mu$m, wherein the weight ratio of (A) to (B) is 1:0.1 to 1:5, (C') an oil phase containing at least 30% by weight, based upon the total oil phase component, of silicone oil, (D) an emulsifying agent having an HLB value of not more than 7, and (E) water. The weight ratio of the mixed powder of (A)+(B) to the oil phase (C') is preferably 1:5 to 1:30, the content of (A)+(B)+(C') is 9.0 to 90.0% by weight, the content of the emulsifying agent (D) having an HLB value of not more than 7 is preferably 0.01 to 5.0% by weight, and the content of the water (E) is preferably 9.0 to 90.0% by weight.

In accordance with the third aspect of the present invention, there is further provided a water-in-oil type emulsion cosmetic composition comprising a mixed powder of (A) an organopolysiloxane elastomer spherical powder having an average particle size of 2.0 to 5.0 $\mu$m and a particle size distribution of 1 to 15 $\mu$m and (B) a hydrophobic silica powder having an average particle size of not more than 0.2 $\mu$m, wherein the weight ratio of (A) to (B) is 1:0.1 to 1:5, (C') an oil phase containing at least 30% by weight, based upon the total oil phase component, of silicone oil, (D) an emulsifying agent having an HLB value of not more than 7, (E) water, and (F) a metallic soap. The weight ratio of the mixed powder of (A)+(B) to the oil phase (C') is preferably 1:5 to 1:30, the content of (A)+(B)+(C') is preferably 4.0 to 90.0% by weight, the content of the emulsifying agent (D) having an HLB value of not more than 7 is 0.01 to 5.0% by weight, the content of the water (E) is 9.0 to 95.0% by weight and the content of the metallic soap (F) is 0.01 to 5.0% by weight, and the average particle size of the emulsion particles is preferably 1.0 to 10.0 $\mu$m and the particle size distribution is 0.1 to 20 $\mu$m.

In accordance with the fourth aspect of the present invention, there is still further provided a water-in-oil type emulsion cosmetic composition comprising a mixed powder of (A) an organopolysiloxane elastomer spherical powder having an average particle size of 2.0 to 5.0 $\mu$m and a particle size distribution of 1 to 15 $\mu$m and (B) a hydrophobic silica powder having an average particle size of not more than 0.2 $\mu$m, wherein the weight ratio of (A) to (B) is 1:0.1 to 1:5, (C') an oil phase containing at least 30% by weight, based upon the total oil phase component, of silicone oil, (D) an emulsifying agent having an HLB value of not more than 7, (E) water, and (G) an organically modified clay mineral. The weight ratio of the mixed powder of (A)+(B) to the oil phase (C') is preferably 1:4 to 1:40, the content of (A)+(B)+(C') is preferably 4.0 to 90.0% by weight, the content of the emulsifying agent (D) having an HLB value of not more than 7 is preferably 0.01 to 5.0% by weight, the content of the water (E) is preferably 9.0 to 95.0% by weight, the content of the organically modified clay mineral (G) is preferably 0.01 to 5.0% by weight, the average particle size of the emulsion particles is preferably 1.0 to 20.0 $\mu$m and the particle size distribution is preferably 0.1 to 30 $\mu$m.

DESCRIPTION OF THE PREFERRED EMBODIMENTS

The present invention was made in consideration of the above-mentioned problems in the prior art. The present inventors engaged in repeated in-depth studies and, as a result, found that by using a mixed powder of a powder having a high oil absorption and a powder having a different particle size combined in a specific ratio of weight and by using a metallic soap as an emulsifying adjuvant they could obtain a water-in-oil type emulsion with a good spreadability, a fresh feeling in use, and stability, whereby the present invention has been completed.

The present invention will now be explained in detail.

The organopolysiloxane elastomer in the form of a spherical powder having an average particle size of 2.0 to 5.0 μm and a particle size distribution of 1 to 15 μm usable as the component (A) of the present invention are given, in detail, in Japanese Examined Patent Publication (Kokoku) No. 4-66446, Japanese Unexamined Patent Publication (Kokai) No. 2-243612, and Japanese Examined Patent Publication (Kokoku) No. 4-17162. As commercially available products, for example, Torayfil E-505C and Torayfil E-506C (brandnames of Toray-Dow Corning Silicone Co.) may be mentioned.

The hydrophobic silica powder having the average particle size of not more than 0.2 μm usable, as the component (B) of the present invention, is one having the trimethylsilylated or dimethylsilylated hydrophilic hydroxy groups on the surface thereof. More specifically, among trimethylsilylated silica powders, AEROSIL R813 (brandname of Nippon Aerosil Co.) and, among dimethylsilylated silica powders, AEROSIL R972 and R974 (brandnames of Nippon Aerosil Co.) etc., may be mentioned.

The component (A) and component (B) are used in the form of a mixture. The range is a weight ratio of (A) to (B) of 1:0.1 to 1:5, preferably 1:0.1 to 1:3. If the ratio (B):(A) is less than 0.1:1, the result is a poor stability, while if the ratio (B):(A) is more than 5:1, the result is unpreferable stickiness in the feeling in use.

In the present invention, an oil phase (C) is used. Especially, an oil phase (C') should contain at least 30% by weight, based upon the total oil phase components, of a silicone oil. This silicone oil is preferably used for improving the feeling in use.

Examples of the silicone oil mixed in the present W/O type emulsion cosmetic composition are methylpolysiloxane, methylphenylpolysiloxane, cyclic dimethylpolysiloxane (e.g., octamethylcyclotetrasiloxane, tetramethyltetrahydrogenpolysiloxane, dodecamethylcyclohexasiloxane), methylhydrogenpolysiloxane, decamethylpolysiloxane, dimethylpolysiloxane, highly polymerized methylpolysiloxane, amino acid modified silicone, etc. These silicone oils are mixed, when used, into the total oil phase in an amount of preferably at least 30% by weight. When an amount of the silicone oil is less than 30% by weight, a fresh feeling in use cannot be desirably improved.

The preferable silicone oils are dimethylpolysiloxane having a viscosity of 0.65–5000 cst at 25° C., methylphenylpolysiloxane having a viscosity of 10–1000 cst at 25° C.

The oil phase component (C) other than the silicone oils, usable in the present invention, include for example, as plant and animal oils, natural plant and animal oils such as avocado oil, tsubaki (camellia japonica L.) oil, macademia nut oil, corn oil, evening primrose oil, jojoba oil, mink oil, rapeseed oil, castor oil, sunflower oil, cacao oil, coconut oil, rice bran oil, olive oil, lanolin, squalene; oil and fatty acid esters such as liquid paraffin, squalane, isopropyl myristate, isopropyl palmitate, isopropyl stearate, glycerol 2-ethylhexanoate, glyceryl tri-2-ethylhexanoate, pentaerythritol tetra-2-ethylhexanoate; polar oils such as diethylene glycol monopropyl ether, polyoxyethylene polyoxypropylene pentaerythritol ether, polyoxypropylene butyl ether, ethyl linolate, and the like.

These oil components are preferably mixed in a weight ratio of the mixed powder (A)+(B) to (C) or (C') of 1:5 to 1:30, more preferably 1:6 to 1:20. If (C) or (C'): (A)+(B) is less than 5:1 and if more than 30:1, the stability of the emulsion tends to deteriorate. In the present invention, the amount of (A)+(B)+(C) or (C') contained is preferably 9.0 to 90.0% by weight in the first and second aspects and 4.0 to 90.0% by weight in the third and fourth aspects.

The emulsifying agent (D) having an HLB of not more than 7, usable as the component (D) mixed in the water-in-oil type emulsion of the present invention include, for example, sorbitan fatty acid esters such as sorbitan monolaurate, sorbitan monooleate, sorbitan monoisostearate, sorbitan tristearate; glycerol fatty acid esters such as, glycerol monostearate, glycerol monooleate, glycerol isostearate; polyoxyethylene hydrogenated caster oils such as, POE (5), POE (7.5), POE (10) hydrogenated castor oil polyether silicon surfactants etc.

Among the above emulsifying agents, the polyether silicon surfactants such as those having the following formula (I) are preferable.

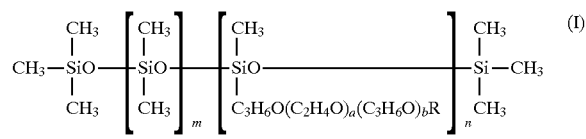

wherein R represents hydrogen atom or an alkyl group having 1 to 5 carbon atoms, m is 1 to 150 on average, n is 1 to 50 on average, and a and b are independently 0 to 35 on average.

The content of the component (D) is preferably 0.01 to 5.0% by weight of the total composition, more preferably 0.1 to 3.0% by weight. When the content of the component (D) is less than 0.01% by weight, there is a case that it is difficult to stabilize the water-in-oil type emulsion of the present invention, while when more than 5.0% by weight, a strong sticky feeling in use is likely resulted.

The metallic soap (F) mixed in the third aspect of the present invention is used as an emulsifying adjuvant and may be a metal salt of a saturated or unsaturated fatty acid. A fatty acid having 10 to 22 carbon atoms, preferably 12 to 18, is preferred. Further, as the salts, for example, aluminum, calcium, magnesium, zinc, etc. may be mentioned. Among them, those particularly preferable as emulsifying adjuvants are aluminum stearate, aluminum myristate, aluminum dioleate, zinc stearate, zinc myristate, zinc oleate, etc.

These metallic soaps are preferably contained in the total amount of the composition in an amount of 0.01 to 5.0% by weight, more preferably 0.05 to 5.0% by weight. When this amount is less than 0.01% by weight, it is difficult to stabilize the water-in-oil emulsion of the present invention as intended, while when more than 5.0% by weight, the spreadability (or slip) at the time of use becomes heavy and an extremely high stickiness is resulted.

In the water-in-oil type emulsion according to the third aspect of the present invention, a fresh feeling in use is given by adjusting the size of the emulsion particles to an average particle size of preferably 1.0 to 20.0 μm and a particle size distribution of preferably 0.1 to 30.0 μm, preferably an average particle size of 1.0 to 10.0 μm and a particle size distribution of 1.0 to 20.0 μm. When the size of the emulsion particles is more than 20 μm, an extremely fresh feeling in use can be obtained, but the stability easily deteriorates along with time, while when less than 0.1 μm, it is difficult to obtain a fresh feeling in use.

The organically modified clay minerals (G) formulated into the fourth aspect of the present invention include colloidal aluminum silicate hydrate having a three layer structure generally having the following structure:

$$(X, Y)_{2-3}(Si, Al)_4O_{10}(OH)_2Z_{1/3} \cdot nH_2O$$

wherein X=Al, Fe(III), Mn(III), Cr(III)
Y=Mg, Fe(II), Ni, Zn, Li
Z=K, Na, Ca

Typically, clay minerals are treated with, for example, quaternary ammonium salt based cationic surfactants having the following structure.

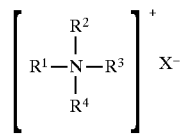

wherein $R^1$ represents a $C_{10}$–$C_{22}$ alkyl or benzyl group, $R^2$ represents a methyl or $C_{10}$–$C_{22}$ alkyl group, $R^3$ and $R^4$ independently a $C_1$–$C_3$ alkyl or hydroxylalkyl group, X represents a halogen atom or a methyl sulfate residue.

The clay minerals to be modified include, for example, natural or synthetic (i.e., the OH group is substituted with fluorine) montmorillonites such as montmorillonite, saponite and hectorite (e.g., commercially available products such as Veegum, Kunipia, Laponite, etc.,) and synthetic mica such as sodium silicic mica, sodium or lithium teniorite (e.g., commercially available products such as Dimonite available from Topy Kogyo K.K.).

Examples of quaternary ammonium salt based surfactants are dodecyltrimethylammonium chloride, myristyltrimethylammonium chloride, cetyltrimethylammonium chloride, stearyltrimethylammonium chloride, arachidyltrimethylammonium chloride, behenyltrimethylammonium chloride, myristyldimethylethylammonium chloride, cetyldimethylethylammonium chloride, stearyldimethylethylammonium chloride, arachidyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcethylammonium chloride, benzylmethylethylstearylammonium chloride, dibehenyldihydroxyethylammonium chloride and the corresponding bromides, and, further dipalmitylpropylethylammonium methylsulfate, etc. These quaternary ammonium salts may be used alone or in any combination thereof.

Typical examples of the organically modified clay minerals are dimethylalkylammonium hectorite, benzylmethylstearylammonium hectorite, aluminum magnesium silicate modified with distearyldimethylammonium chloride, etc. As commercially available products, Benton 38 (Montomorillonite modified with distearyldimethylammonium chloride, available from National Lead Co.).

The organically modified montmorillonite clay minerals may be used in an amount of preferably 0.01 to 1.0% by weight, more preferably 0.05 to 0.5% by weight, based upon the total amount of the O/W type emulsion cosmetic composition of the present invention. When the amount is less than 0.01% by weight, the intended sufficient stability is not easy to obtain, whereas when more than 1.0% by weight, the stability or useability is likely to be impaired.

The water, usable as the component (E) of the present invention is included in an amount of 9.0 to 90.0% by weight in the first and second aspects of the present invention and 9.0 to 95.0% by weight in the third and fourth aspects of the present invention, of the total composition.

The water-in-oil type emulsion of the present invention has the microstructure of ultrafine particles of hydrophobic silica powder and organopolysiloxane elastomer spherical powder with emulsion particles stabilized by the powder of the emulsifying adjuvant metallic soap. When the emulsion is spread on the skin, the powder around the emulsion particles repels moisture, and therefore, the spreadability (or slip) on the skin can give an extremely good feeling in use.

The water-in-oil type emulsion of the present invention may contain, in addition to the above-mentioned components, UV absorbants such as para-aminobenzoic acid, homomethyl-7N-acetylalantoylanylate, butylmethoxybenzoylmethane, glyceryl diparamethoxycinnamate-mono-2-ethylhexanoate, amylsalicylate, octylcinnamate, 2,4-dihydroxybenzophenone; humectants such as glycerol, 1,3-butylene glycol, polyethylene glycol, sorbitol, xylitol, maltitol; thickeners such as methylcellulose, gum arabic, polyvinyl alcohol, montmorillonite, laponite; antioxidants such as butylhydroxytoluene, tocopherol, phitic acid; antibacterial preservatives such as benzoic acid, salicylic acid, sorbic acid, paraoxybenzoic acid alkylesters (ethyl parabene, butyl parabene, etc.), hexachlorophene; acylsarcosinic, for example, sodium Sodium Lauroyl Sarcosinate; organic acids such as glutathione, citric acid, malic acid, succinic acid, lactic acid; vitamin Bs such as vitamin A and its derivatives, vitamin $B_6$ hydrogenchloride, vitamin $B_6$ tripalmitate, vitamin $B_6$ dioctanoate, vitamin $B_2$ and its derivatives, vitamin $B_{12}$, vitamin $B_{15}$ and its derivatives; vitamin Cs such as ascorbic acid, ascorbyl sulfate (salts), ascorbyl phosphate (salts), ascorbyl dipalmitate; vitamin Es such as α-tocopherol, β-tocopherol, γ-tocopherol, vitamin E-acetate, vitamin E-nicotinate; other vitamins such as vitamin Ds, vitamin Hs, pantothenic acid, pantothetine; various drugs such as amide nicotinate, benzyl nicotinate, γ-orysanol, allantoin, glycylrhizic acid (salt), glycylrhezic acid and its derivatives, hinokitiol, musidine, bisabolol, eucalyptol, thymolinositol, pantothelethyl ether, ethynylestradiol, cepharanthine, placenta extract; natural extracts and colors etc., obtained by extraction by organic solvents, alcohol, polyhydric alcohols, water, aqueous alcohols, etc., such as, for example, sorrel, sophora angustifolia, candock, orange, sage, siberian milfoil (*Achillea sibirica*), mallow, Cnidium officinale, Japanese green gentian (*Swertia japonica*), thyme, Angelica acutiloba, Japanese spruce, birch, field horsetail, dishcloth gourd, horse chestnut, mother of thousands (*Saxifraga stolonifera*), arnica, lily, mugwort (*Artemisia princeps*), peony (*Paeonia lactiflora*), aloe, gardenia (*Gardenia jasminoides*), sawara cypress; and the like to an extent not detracting from the effect of the present invention.

EXAMPLES

The present invention will now be further illustrated by, but is by no means limited to, the following Examples, wherein all parts and percentages are expressed on a weight basis unless otherwise noted.

Example I

Evaluation Method

A panel composed of about 10 female experts was used to evaluate the usability based on the following evaluation criteria:

(1) Feeling of Use
  A. Spreadability on skin
    @: Extremely good spreadability
    ○: Good spreadability
    Δ: Somewhat good spreadability
    x: Poor spreadability (slip)

B. Stickiness
   @: Extremely little stickiness
   o: Little stickiness
   Δ: Somewhat sticky
   x: Sticky (2) Stability of Emulsion A cream was allowed to stand for one month at 50° C., 37° C., room temperature, and 0° C. and the stability was evaluated as follows:

@: No abnormalities in appearance
   o: Some slight appearance of oil
   Δ: Appearance of oil
   x: Separation Examples I-1 to I-6 and Comparative Examples I-1 to I-8

The formulations listed in Tables I-1 to I-2 were used to prepare emulsions which were evaluated as to their feeling in use and the stability of the emulsions. The results are shown in Table I-3. Note that, as the organopolysiloxane elastomer spherical powder, Torayfil E-505C was used.

TABLE I-1

| Component (%) | Example | | | | | |
|---|---|---|---|---|---|---|
| | I-1 | I-2 | I-3 | I-4 | I-5 | I-6 |
| Squalane | 10.0 | 10.0 | 10.0 | 10.0 | 10.0 | 10.0 |
| Vaserine | — | — | — | — | — | — |
| Microcrystalline wax | — | — | — | — | — | — |
| Isopropyl myristate | 5.0 | 5.0 | 5.0 | 5.0 | 5.0 | 5.0 |
| Cetyl 2-ethylhexanoate | 10.0 | 10.0 | 10.0 | 10.0 | 10.0 | 10.0 |
| Decamethylcyclopentasiloxane | 5.0 | 5.0 | 5.0 | 5.0 | 5.0 | 5.0 |
| Organopolysiloxane elastomer spherical powder | 2.0 | 3.5 | 2.0 | 0.5 | 3.0 | 0.2 |
| Dimethylsilylated silica powder | 1.0 | 0.5 | 2.0 | 2.5 | 2.0 | 0.7 |
| Glycerol isostearate (HLB = 4) | 3.0 | 3.0 | 3.0 | 3.0 | 3.0 | 3.0 |
| Monosodium L-glutamate | 1.0 | 1.0 | 1.0 | 1.0 | 1.0 | 1.0 |
| Purified water | | | Balance | | | |
| Dipropylene glycol | 10.0 | 10.0 | 10.0 | 10.0 | 10.0 | 10.0 |
| Bentone 38 | — | — | — | — | — | — |

TABLE I-2

| Component (%) | Comparative Example | | | | | | | |
|---|---|---|---|---|---|---|---|---|
| | I-1 | I-2 | I-3 | I-4 | I-5 | I-6 | I-7 | I-8 |
| Squalane | 10.0 | 10.0 | 10.0 | 10.0 | 10.0 | 10.0 | 10.0 | 10.0 |
| Vaserine | 5.0 | 5.0 | — | — | — | — | — | — |
| Microcrystalline wax | 5.0 | 2.0 | — | — | — | — | — | — |
| Isopropyl myristate | 5.0 | 5.0 | 5.0 | 5.0 | 5.0 | 5.0 | 5.0 | 5.0 |
| Cetyl 2-ethylhexanoate | 10.0 | 10.0 | 10.0 | 10.0 | 10.0 | 10.0 | 10.0 | 10.0 |
| Decamethylcyclopentasiloxane | 5.0 | 5.0 | 5.0 | 5.0 | 5.0 | 5.0 | 5.0 | 5.0 |
| Organopolysiloxane elastomer spherical powder | — | —7.0 | 3.0 | — | — | 2.0 | 0.3 | |
| Dimethylsilylated silica powder | — | — | — | — | 6.0 | 2.0 | 0.1 | 2.0 |
| Glycerol isostearate (HLB = 4) | 3.0 | 3.0 | 3.0 | 3.0 | 3.0 | 3.0 | 3.0 | 3.0 |
| Monosodium L-glutamate | 1.0 | 1.0 | 1.0 | 1.0 | 1.0 | 1.0 | 1.0 | 1.0 |
| Purified water | | | | Balance | | | | |
| Dipropylene glycol | 10.0 | 10.0 | 10.0 | 10.0 | 10.0 | 10.0 | 10.0 | 10.0 |
| Bentone 38 | — | 2.0 | — | — | — | — | — | — |

TABLE I-3

| Evaluation | (1) Feeling of Use | | (2) Stability of Emulsion | | | |
|---|---|---|---|---|---|---|
| | Spreadability on skin | Stickiness | 0° C. | Room Temp. | 37° C. | 50° C. |
| Example | | | | | | |
| I-1 | @ | @ | @ | @ | @ | @ |
| I-2 | @ | @ | @ | @ | @ | @ |
| I-3 | @ | @ | @ | @ | @ | @ |
| I-4 | @ | @ | @ | @ | @ | @ |
| I-5 | @ | @ | o | @ | @ | o |
| I-6 | @ | o | @ | @ | @ | o |
| Comp. Example | | | | | | |
| I-1 | Δ | Δ | Δ | Δ | Δ | x |
| I-2 | Δ | Δ | @ | @ | o | o |
| I-3 | Δ | @ | @ | @ | o | Δ |
| I-4 | o | @ | o | o | o | Δ |
| I-5 | x | x | o | @ | o | Δ |
| I-6 | Δ | Δ | o | @ | o | Δ |
| I-7 | @ | @ | o | o | o | Δ |
| I-8 | o | o | @ | @ | o | Δ |

Example I-7: Moisturizing Cream

| (1) Purified water | Balance |
|---|---|
| (2) Sodium chloride | 1.0 wt % |
| (3) Sodium lactate | 1.0 |
| (4) Propylene glycol | 10.0 |
| (5) Liquid paraffin | 15.0 |
| (6) Cetyl-2-ethylhexanoate | 10.0 |
| (7) Pentaerythritol tetra-2-ethylhexanoate | 3.0 |
| (8) Methylphenylpolysiloxane | 3.0 |
| (9) Decamethylcyclopentasiloxane | 5.0 |
| (10) Torayfil E-505C | 2.5 |
| (11) Aerosil R972 | 2.0 |
| (12) Glycerol monooleate (HLB = 5.5) | 3.5 |
| (13) Vitamin E acetate | q.s. |
| (14) Methyl parabene | q.s. |
| (15) Perfume | q.s. |

Method of Production (5), (6), (7), (8), (9), (12), (13), and (15), were mixed at room temperature to produce an oil phase into which the powders of (10) and (11) were gradually added and uniformly dispersed. Next, (2) and (3) were dissolved in (1) into was then added (14) dissolved in (4) to obtain an aqueous phase which was then gradually added to the oil phase. This was homogeneously dispersed by a homomixer, then the emulsion granules were made even to obtain a moisturizing cream.

Example I-8: Emulsion

| | | |
|---|---|---|
| (1) Purified water | Balance | |
| (2) Sodium chloride | 0.5 wt % | |
| (3) Sodium glutamate | 0.5 | |
| (4) Propylene glycol | 8.0 | |
| (5) Squalane | 10.0 | |
| (6) Pentaerythritoltetra-2-ethylhexanoate | 15.0 | |
| (7) Methylphenylpolysiloxane | 5.0 | |
| (8) Octamethylcyclotetrasiloxane | 5.0 | |
| (9) Torayfil E-505C | 1.5 | |
| (10) Aerosil R972 | 0.5 | |
| (11) Dimethylpolysiloxane Polyoxyalkylene polymer (HLBL = 3) | 3.0 | |
| (12) Magnesium ascorbyl phosphate | q.s. | |
| (13) Methyl parabene | q.s. | |
| (14) Perfume | q.s. | |

Method of Production (5), (6), (7), (8), (11), and (14) were mixed at room temperature to produce an oil phase into which the powders of (9) and (10) were then gradually added and homogeneously dispersed. Next, (2), (3), and (12) were dissolved in (1) into was then added (13) dissolved in (4) to obtain an aqueous phase which was then gradually added to the oil phase and homogeneously dispersed by a homomixer, then the emulsion granules were made even to obtain an emulsion.

Example I-7: Sunburn Preventing Emulsion

| | | |
|---|---|---|
| (1) Purified water | Balance | |
| (2) Polyethylene glycol 6000 | 1.0 wt% | |
| (3) Propylene glycol | 8.0 | |
| (4) Pentaerythritol tetra-2-ethylhexanoate | 10.0 | |
| (5) Cetyl-2-ethylhexanoate | 5.0 | |
| (6) Squalane | 5.0 | |
| (7) Squalane | 5.0 | |
| (8) Torayfil E-506C | 1.5 | |
| (9) Aerosil R972 | 0.5 | |
| (10) Dimethylpolysiloxane-polyxyalkylene polymer (HLB = 3) | 3.0 | |
| (11) Octylmethoxycinnamate | q.s. | |
| (12) 2,4-dihydroxybenzophenone | q.s. | |
| (13) Methyl parabene | q.s. | |
| (14) Perfume | q.s. | |

Method of Production (4), (5), (6), (7), (10), and (14) were mixed at room temperature to produce an oil phase, followed by mixing thereto (11) and (12) dissolved a part of (4), into which the powders of (8) and (9) were gradually added and homogeneously dispersed. Next, (2) was dissolved in (1) into was then added (13) dissolved in (3) to obtain an aqueous phase which was then gradually added to the oil phase and homogeneously dispersed by a homomixer, then the emulsion granules were made even to obtain a sunburn preventing emulsion.

Example II

Method of Evaluation

A panel composed of about 10 female experts was used to evaluate the usability based on the following evaluation criteria:

(1) Feeling of use

A. Spreadability on skin
@: Extremely good spreadability
o: Good spreadability
Δ: Somewhat good spreadability
x: Poor spreadability B. Stickiness
@: Extremely little stickiness
o: Little stickiness
Δ: Somewhat sticky
x: Sticky C. Refreshing feeling
@: Extremely refreshing
o: Refreshing
Δ: Somewhat refreshing
x: Not refreshing (2) Stability of Emulsion A cream was allowed to stand for one month at 50° C., 37° C., room temperature, and 0° C. and the stability was evaluated.

@: No abnormalities in appearance
o: Some slight appearance of oil
Δ: Appearance of oil
x: Separation Examples II-1 to II-4 and Comparative Examples II-1 to II-6

The formulations listed in Table II-1 and Table II-2 were used to prepare emulsions which were evaluated as to their feeling in use and the stability of the emulsions. The results are shown in Table II-3. Note that as the organopolysiloxane elastomer spherical powder, use was made of Torayfil E-505C.

TABLE II-1

| | Example | | | |
|---|---|---|---|---|
| Component (%) | II-1 | II-2 | II-3 | II-4 |
| Squalane | 5.0 | 5.0 | 5.0 | 5.0 |
| Isopropyl myristate | 5.0 | 5.0 | 5.0 | 5.0 |
| Cetyl 2-ethylhexanoate | 5.0 | 5.0 | 5.0 | 5.0 |
| Decamethylcyclopentasiloxane | 10.0 | 5.0 | 5.0 | 5.0 |
| Dimethylpolysiloxane | 5.0 | 10.0 | 10.0 | 10.0 |
| Organopolysiloxane elastomer spherical powder | 3.0 | 3.5 | 3.5 | 0.2 |
| Dimethylsilylated silica powder | 1.0 | 0.5 | 3.0 | 0.7 |
| Glycerol isostearate (HLB = 4) | 3.0 | 3.0 | 3.0 | 3.0 |
| Monosodium L-glutamate | 1.0 | 1.0 | 1.0 | 1.0 |
| Purified water | Balance | | | |
| Dipropylene glycol | 10.0 | 10.0 | 10.0 | 10.0 |

TABLE II-2

| Component (%) | Comparative Example | | | | | |
|---|---|---|---|---|---|---|
| | II-1 | II-2 | II-3 | II-4 | II-5 | II-6 |
| Squalane | 10.0 | 10.0 | 10.0 | 10.0 | 5.0 | 5.0 |
| Isopropyl myristate | 10.0 | 10.0 | 10.0 | 10.0 | 5.0 | 5.0 |
| Cetyl 2-ethylhexanoate | 10.0 | 10.0 | 5.0 | 5.0 | 5.0 | 5.0 |
| Decamethylcyclopentasiloxane | — | — | — | — | 10.0 | 10.0 |
| Dimethylpolysiloxane | — | — | 5.0 | 5.0 | 5.0 | 5.0 |
| Organopolysiloxane elastomer spherical powder | 3.0 | 3.0 | 3.0 | 3.0 | 2.0 | 0.3 |
| Dimethylsilylated silica powder | 1.0 | 0.1 | 1.0 | 0.1 | 0.1 | 2.0 |
| Glycerol isostearate (HLB = 4) | 3.0 | 3.0 | 3.0 | 3.0 | 3.0 | 3.0 |
| Monosodium L-glutamate | 1.0 | 1.0 | 1.0 | 1.0 | 1.0 | 1.0 |
| Purified water | Balance | | | | | |
| Dipropylene glycol | 10.0 | 10.0 | 10.0 | 10.0 | 10.0 | 10.0 |

TABLE II-3

| Evaluation | (1) Feeling of Use | | | (2) Stability of Emulsion | | | |
|---|---|---|---|---|---|---|---|
| | Spreadability | Stickiness | Refreshing feeling | 0° C. | Room Temp. | 37° C. | 50° C. |
| Example | | | | | | | |
| II-1 | ⊚ | ⊚ | ⊚ | ⊚ | ⊚ | ⊚ | ⊚ |
| II-2 | ⊚ | ⊚ | ⊚ | ⊚ | ⊚ | ⊚ | ⊚ |
| II-3 | ⊚ | ⊚ | ⊚ | ○ | ⊚ | ⊚ | ⊚ |
| II-4 | ⊚ | ⊚ | ⊚ | ⊚ | ⊚ | ⊚ | ○ |
| Comp. Example | | | | | | | |
| II-1 | ○ | ○ | x | ⊚ | ⊚ | ⊚ | ⊚ |
| II-2 | ○ | ○ | x | ⊚ | ⊚ | ○ | ○ |
| II-3 | ○ | ⊚ | Δ | ⊚ | ⊚ | ⊚ | ⊚ |
| II-4 | ⊚ | ⊚ | Δ | ⊚ | ⊚ | ○ | ○ |
| II-5 | ⊚ | ⊚ | ⊚ | ⊚ | ⊚ | ○ | Δ |
| II-6 | ⊚ | Δ | Δ | ⊚ | ⊚ | ○ | Δ |

Example II-5: Moisturizing Cream

| (1) Purified water | Balance |
|---|---|
| (2) Sodium lactate | 1.0 wt % |
| (3) 1,3-butylene glycol | 5.0 |
| (4) Liquid paraffin | 5.0 |
| (5) Cetyl-2-ethylhexanoate | 5.0 |
| (6) Pentaerythritol tetra-2-ethylhexanoate | 3.0 |
| (7) Methylphenylpolysiloxane | 3.0 |
| (8) Decamethylcyclopentasiloxane | 10.0 |
| (9) Torayfil E-505C | 2.5 |
| (10) Aerosil R972 | 2.0 |
| (11) Silicone SC9450N (made by Shinetsu Silicone, HLB = 4.5) | 2.0 |
| (12) Vitamin E acetate | 3.0 |
| (13) Methyl parabene | q.s. |
| (14) Perfume | q.s. |

Method of Production (4), (5), (6), (7), (8), (11), (12), and (14) were mixed at room temperature to produce an oil phase into which the powders of (9) and (10) were gradually added and uniformly dispersed. Next, (2) was dissolved in (1) into was then added (13) dissolved in (3) to obtain an aqueous phase which was then gradually added to the oil phase. This was homogeneously dispersed by a homomixer, then the emulsion granules were made even to obtain a moisturizing cream.

Example II-6: Emulsion

| (1) Purified water | Balance |
|---|---|
| (2) Sodium chloride | 1.0 wt % |
| (3) Polyethylene glycol 11000 | 1.0 |
| (4) Propylene glycol | 8.0 |
| (5) Squalane | 5.0 |
| (6) Pentaerythritol tetra-2-ethylhexanoate | 5.0 |
| (7) Methylphenylpolysiloxane | 5.0 |
| (8) Octamethylcyclotetrasiloxane | 15.0 |
| (9) Torayfil E-505C | 2.0 |
| (10) Aerosil R972 | 0.5 |
| (11) Silicone SC9450N (made by Shinetsu Silicone, HLB = 4.5) | 3.0 |
| (12) Magnesium ascorbyl phosphate | 1.0 |
| (13) Methyl parabene | q.s. |
| (14) Perfume | q.s. |

Method of Production (5), (6), (7), (8), (11), (14) were mixed at room temperature to produce an oil phase into which the powders of (9) and (10) were then gradually added and homogeneously dispersed. Next, (2), (3), and (12) were dissolved in (1) into was then added (13) dissolved in (4) to obtain an aqueous phase which was then gradually added to the oil phase and homogeneously dispersed by a homomixer, then the emulsion granules were made even to obtain an emulsion.

Example II-7: Sunburn Preventing Emulsion

| (1) Purified water | Balance |
|---|---|
| (2) Polyethylene glycol 6000 | 1.0 wt % |
| (3) Sodium glutamate | 1.0 |
| (4) Propylene glycol | 8.0 |
| (5) Pentaerythritol tetra-2-ethylhexanoate | 10.0 |
| (6) Cetyl-2-ethylhexanoate | 5.0 |
| (7) Methylphenylpolysiloxane | 5.0 |
| (8) Decamethylcyclopentasiloxane | 15.0 |
| (9) Torayfil E-506C | 2.0 |
| (10) Aerosil R972 | 0.5 |
| (11) Silicone SC9450N (made by Shinetsu Silicone, HLB = 4.5) | 1.0 |
| (12) Diglycerol monooleate (HLB = 6.5) | 2.0 |
| (13) Octylmethoxycinnamate | q.s. |
| (14) 2,4-dihydroxybenzophenone | q.s. |
| (15) Methyl parabene | q.s. |
| (16) Perfume | q.s. |

Method of Production (5), (6), (7), (8), (11), (12), (13), (14), and (16) were mixed at room temperature to produce an oil phase into which the powders of (9) and (10) were gradually added and homogeneously dispersed. Next, (2) and (3) were dissolved in (1) into which was then added (15) dissolved in (4) to obtain an aqueous phase which was then gradually added to the oil phase and homogeneously dispersed by a homomixer, then the emulsion granules were made even to obtain a sunburn preventing emulsion.

Example III

Evaluation Method

A panel composed of about 10 female experts was used to evaluate the usability based on the following evaluation criteria:

(1) Feeling of use
A. Spreadability on skin
  @: Extremely good spreadability
  o: Good spreadability
  Δ: Somewhat good spreadability
  x: Poor spreadability
B. Stickiness
  @: Extremely little stickiness
  o: Little stickiness
  Δ: Somewhat sticky
  x: Sticky
C. Refreshing feeling
  @: Extremely refreshing
  o: Refreshing
  Δ: Somewhat refreshing
  x: Not refreshing (2) Stability of Emulsion A cream was allowed to stand for one month at 50° C., 37° C., room temperature, and 0° C. and the stability was evaluated.
  @: No abnormalities in appearance
  o: Some slight appearance of oil
  Δ: Appearance of oil
  x: Separation Examples III-1 to III-6 and Comparative Examples III-1 and III-2

The formulations listed in Table III-1 and Table III-2 were used to prepare emulsions which were evaluated as to their feeling in use and the stability of the emulsions. Further, the average particle size and particle size distribution of the emulsion particles were measured. The results are shown in Table III-3. Note that, as the organopolysiloxane elastomer spherical powder, Torayfil E-505C was used.

TABLE III-1

| Component (%) | Examples | | | | | |
|---|---|---|---|---|---|---|
| | III-1 | III-2 | III-3 | III-4 | III-5 | III-6 |
| Squalane | 5.0 | 4.0 | 5.0 | 5.0 | 5.0 | 4.0 |
| Isopropyl myristate | 5.0 | 4.0 | 5.0 | 2.0 | 5.0 | 4.0 |
| Cetyl 2-ethylhexanoate | 5.0 | 1.0 | 5.0 | 8.0 | 5.0 | 1.0 |
| Decamethylcyclopenta-siloxane | 10.0 | 5.0 | 5.0 | 5.0 | 10.0 | 5.0 |
| Methylphenylpolysiloxane | 5.0 | 10.0 | 10.0 | 10.0 | 5.0 | 10.0 |
| Organopolysiloxane elastomer spherical powder | 3.0 | 3.5 | 0.8 | 3.5 | 3.0 | 3.5 |
| Dimethylsilylated silica powder | 1.0 | 0.5 | 0.8 | 0.5 | 1.0 | 0.5 |
| Glycerol isostearate (HLB = 4) | 0.5 | 1.0 | 1.0 | 1.0 | 0.1 | 0.5 |
| Zinc stearate | 3.0 | 2.0 | 5.0 | 0.01 | 3.0 | 10.0 |
| Monosodium L-glutamate | 1.0 | 1.0 | 1.0 | 1.0 | 1.0 | 1.0 |
| Purified water | Bal. | Bal. | Bal. | Bal. | Bal. | Bal. |
| Dipropylene glycol | 10.0 | 10.0 | 10.0 | 10.0 | 10.0 | 10.0 |

TABLE III-2

| Component (%) | Comparative Examples | |
|---|---|---|
| | III-1 | III-2 |
| Squalane | 5.0 | 4.0 |
| Isopropyl myristate | 5.0 | 4.0 |
| Cetyl 2-ethylhexanoate | 5.0 | 1.0 |

TABLE III-2-continued

| Component (%) | Comparative Examples | |
|---|---|---|
| | III-1 | III-2 |
| Decamethylcyclopentasiloxane | 10.0 | 5.0 |
| Methylphenylpolysiloxane | 5.0 | 10.0 |
| Organopolysiloxane elastomer spherical powder | 3.0 | 3.5 |
| Dimethylsilylated silica powder | 1.0 | 0.5 |
| Glycerol isostearate (HLB = 4) | 1.0 | 2.0 |
| Zinc stearate | — | — |
| Monosodium L-glutamate | 1.0 | 1.0 |
| Purified water | Bal. | Bal. |
| Dipropylene glycol | 10.0 | 10.0 |

TABLE III-3

| Evaluation | (1) Feeling of use | | | (2) Stability of emulsion | | | | Emulsion particles (μm) | |
|---|---|---|---|---|---|---|---|---|---|
| | Spreadability (slip) | Stickiness | Refreshfeeling | 0° C. | Room temp. | 37° C. | 50° C. | Average particle size | Particle-size distribution |
| Ex. III-1 | @ | @ | @ | @ | @ | @ | @ | 1–5 | 0.1–15 |
| Ex. III-2 | @ | @ | @ | @ | @ | @ | @ | 1–5 | 0.1–20 |
| Ex. III-3 | @ | o | @ | @ | @ | @ | @ | 1–5 | 0.1–20 |
| Ex. III-4 | @ | @ | @ | @ | @ | @ | @ | 1–5 | 0.1–15 |
| Ex. III-5 | @ | @ | o | o | @ | o | o | 1–2 | 0.1–5 |
| Ex. III-6 | @ | o | o | @ | @ | o | o | 5–20 | 1–50 |
| Comp. Ex. III-1 | @ | o | Δ | @ | @ | @ | o | 1–5 | 0.1–15 |
| Comp. Ex. III-2 | @ | o | Δ | @ | @ | o | Δ | 5–20 | 1–50 |

Example III-5: Moisturizing Cream

| | |
|---|---|
| (1) Purified water | Balance |
| (2) Polyethylene glycol 400 | 1.0 wt % |
| (3) Sodium lactate | 1.0 |
| (4) 1,3-butylene glycol | 5.0 |
| (5) Liquid paraffin | 5.0 |
| (6) Cetyl-2-ethylhexanoate | 5.0 |
| (7) Pentaerythritol tetra-2-ethylhexanoate | 3.0 |
| (8) Methylphenylpolysiloxane | 3.0 |
| (9) Decamethylcyclopentasiloxane | 10.0 |
| (10) Torayfil E-505C | 2.5 |
| (11) Aerosil R972 | 2.0 |
| (12) Silicone SC9450N (made by Shinetsu Silicone, HLB = 4.5) | 1.0 |
| (13) Zinc stearate | 2.0 |
| (14) Vitamin E acetate | 3.0 |
| (15) Methyl parabene | q.s. |
| (16) Perfume | q.s. |

Method of Production (5), (6), (7), (8), (9), (12), (13), (14), (15), and (16) were mixed at room temperature to produce an oil phase into which the powders of (10) and (11) were gradually added and uniformly dispersed. Next, (2) and (3) were dissolved in (1) into was then added (15) dissolved in (4) to obtain an aqueous phase which was then gradually added to the oil phase. This was homogeneously dispersed by a homomixer, then the emulsion granules were made even to obtain a moisturizing cream.

Example III-6: Emulsion

| | | |
|---|---|---|
| (1) | Purified water | Balance |
| (2) | Sodium chloride | 1.0 wt % |
| (3) | Trimethylglycerol | 5.0 |
| (4) | Propylene glycol | 8.0 |
| (5) | Squalane | 5.0 |
| (6) | Pentaerythritol tetra-2-ethylhexanoate | 5.0 |
| (7) | Methylphenylpolysiloxane | 5.0 |
| (8) | Octamethylcyclotetrasiloxane | 15.0 |
| (9) | Torayfil E-505C | 2.0 |
| (10) | Aerosil R972 | 0.5 |
| (11) | Silicone SC9450N (made by Shinetsu Silicone, HLB = 4.5) | 3.0 |
| (12) | Aluminum stearate | 0.5 |
| (13) | Magnesium ascorbyl phosphate | 4.0 |
| (14) | Methyl parabene | q.s. |
| (15) | Perfume | q.s. |

Method of Production (5), (6), (7), (8), (11), (12), and (15) were mixed at room temperature to produce an oil phase into which the powders of (9) and (10) were then gradually added and homogeneously dispersed. Next, (2), (3), and (13) were dissolved in (1) into was then added (14) dissolved in (4) to obtain an aqueous phase which was then gradually added to the oil phase and homogeneously dispersed by a homomixer, then the emulsion granules were made even to obtain an emulsion.

Example III-7: Sunburn Preventing Emulsion

| | | |
|---|---|---|
| (1) | Purified water | Balance |
| (2) | Glycerol | 1.0 wt % |
| (3) | Sodium glutamate | 1.0 |
| (4) | Propylene glycol | 8.0 |
| (5) | Pentaerythritol tetra-2-ethylhexanoate | 1.0 |
| (6) | Cetyl-2-ethylhexanoate | 1.0 |
| (7) | Methylphenylpolysiloxane | 5.0 |
| (8) | Decamethylcyclopentasiloxane | 15.0 |
| (9) | Torayfil E-506C | 3.0 |
| (10) | Aerosil R972 | 0.5 |
| (11) | Silicone SC9450N (made by Shinetsu Silicone, HLB = 4.5) | 1.0 |
| (12) | Diglycerol monoisostearate (HLB = 5.5) | 1.0 |
| (13) | Magnesium stearate | 2.0 |
| (14) | Octylmethoxycinnamate | 10.0 |
| (15) | 2,4-dihydroxybenzophenone | 3.0 |
| (16) | Methyl parabene | q.s. |
| (17) | Perfume | q.s. |

Method of Production (5), (6), (7), (8), (11), (12), (13), (14), (15), and (17) were mixed at room temperature to produce an oil phase into which the powders of (9) and (10) were gradually added and homogeneously dispersed. Next, (2) and (3) were dissolved in (1) into was then added (16) dissolved in (4) to obtain an aqueous phase which was then gradually added to the oil phase and homogeneously dispersed by a homomixer, then the emulsion granules were made even to obtain a sunburn preventing emulsion.

Example IV

Method of Evaluation

A panel composed of about 10 female experts was used to evaluate the usability based on the following evaluation criteria:

(1) Feeling of use

A. Spreadability (slip) on skin
@: Extremely good spreadability
o: Good spreadability
Δ: Somewhat good spreadability
x: Poor spreadability B. Stickiness
@: Extremely little stickiness
o: Little stickiness
Δ: Somewhat sticky
x: Sticky C. Refreshing feeling
Δ: Extremely refreshing
o: Refreshing
Δ: Somewhat refreshing
x: Not refreshing (2) Stability of Emulsion A cream was allowed to stand for one month at 50° C., 37° C., room temperature, and 0° C. and the stability was evaluated.

@: No abnormalities in appearance
o: Some slight appearance of oil
Δ: Appearance of oil
x: Separation Examples IV-1 to IV-6 and Comparative Examples IV-1 and IV-2

The formulations listed in Table IV-1 and Table IV-2 were used to prepare emulsions which were evaluated as to their feeling in use and the stability of the emulsions. Further, the average particle size and distribution of particle size of the emulsion particles were measured. The results are shown in Table IV-3 and Table IV-4. Note that as the organopolysiloxane elastomer spherical powder, use was made of Torayfil E-506C.

TABLE IV-1

| | Example | | | | | |
|---|---|---|---|---|---|---|
| Component (%) | IV-1 | IV-2 | IV-3 | IV-4 | IV-5 | IV-6 |
| Squalane | 5.0% | 4.0% | 5.0% | 5.0% | 5.0% | 4.0% |
| Isopropyl myristate | 5.0 | 4.0 | 5.0 | 2.0 | 5.0 | 4.0 |
| Cetyl 2-ethylhexanoate | 5.0 | 1.0 | 5.0 | 8.0 | 5.0 | 1.0 |
| Decamethylcyclopenta-siloxane | 10.0 | 5.0 | 5.0 | 5.0 | 10.0 | 15.0 |
| Methylpolysiloxane | 5.0 | 5.0 | 5.0 | 5.0 | 5.0 | 5.0 |
| Organopolysiloxane elastomer spherical powder | 3.0 | 0.5 | 0.8 | 2.5 | 2.5 | 2.5 |
| Dimethylsilylated silica powder | 1.0 | 2.0 | 0.8 | 0.5 | 0.5 | 0.5 |
| Glycerol isostearate (HLB = 4) | 0.5 | 1.0 | 1.0 | 1.0 | 0.3 | 0.5 |
| Organically modified clay minerals | 0.07 | 0.7 | 1.0 | 0.01 | 0.1 | 1.0 |

TABLE IV-1-continued

| | Example | | | | | |
|---|---|---|---|---|---|---|
| Component (%) | IV-1 | IV-2 | IV-3 | IV-4 | IV-5 | IV-6 |
| Sodium lactate | 1.0 | 1.0 | 1.0 | 1.0 | 1.0 | 1.0 |
| Purified water | | | Balance | | | |
| Dipropylene glycol | 10.0 | 10.0 | 10.0 | 10.0 | 10.0 | 10.0 |

TABLE IV-2

| | Comparative Examples | | | |
|---|---|---|---|---|
| Component (%) | IV-1*[1] | IV-2 | IV-3 | IV-4 |
| Squalane | 5.0% | 4.0% | 5.0% | 5.0% |
| Isopropyl myristate | 5.0 | 4.0 | 5.0 | 2.0 |
| Cetyl 2-ethylhexanoate | 5.0 | 1.0 | 5.0 | 8.0 |
| Decamethylcyclopentasiloxane | 10.0 | 5.0 | 5.0 | 5.0 |
| Methylpolysiloxane | 5.0 | 5.0 | 5.0 | 5.0 |
| Organopolysiloxane elastomer spherical powder | 3.0 | 3.5 | 3.0 | 3.5 |
| Dimethylsilylated silica powder | 1.0 | 0.5 | 1.0 | 0.5 |
| Glycerol isostearate (HLB = 4) | 1.0 | 1.0 | 1.0 | 1.0 |
| Organically modified clay minerals | — | — | 0.005 | 2.0 |
| Sodium lactate | 1.0 | 1.0 | 1.0 | 1.0 |
| Purified water | | Balance | | |
| Dipropylene glycol | 10.0 | 10.0 | 10.0 | 10.0 |

*[1]Reference Example

TABLE IV-3

| | Example | | | | | |
|---|---|---|---|---|---|---|
| Evaluation | IV-1 | IV-2 | IV-3 | IV-4 | IV-5 | IV-6 |
| Feeling of Use | | | | | | |
| Spreadability on skin | ◎ | ◎ | ◎ | ◎ | ○ | ◎ |
| Stickiness | ◎ | ◎ | ◎ | ◎ | ◎ | ◎ |
| Refreshing feeling | ◎ | ◎ | ◎ | ◎ | ○ | ◎ |
| Emulsion particle (μ) | | | | | | |
| Ave. particle diameter | 1–5 | 1–10 | 1–5 | 1–5 | 1–2 | 5–30 |
| Particle size dist. | 0.1–15 | 0.1–20 | 0.1–15 | 0.1–20 | 0.1–10 | 1–50 |
| 0° C. | ◎ | ◎ | ◎ | ◎ | ◎ | ○ |
| Room temp. | ◎ | ◎ | ◎ | ◎ | ◎ | ◎ |
| 37° C. | ◎ | ◎ | ◎ | ◎ | ○ | ○ |
| 50° C. | ◎ | ◎ | ◎ | ◎ | ○ | ○ |

TABLE IV-4

| | Comparative Example | | | |
|---|---|---|---|---|
| Evaluation | IV-1 | IV-2 | IV-3 | IV-4 |
| Feeling of Use | | | | |
| Spreadability on skin | ◎ | ◎ | ◎ | Δ |
| Stickiness | ◎ | ◎ | ◎ | ○ |
| Refreshing feeling | ◎ | ◎ | ◎ | ○ |
| Emulsion particle (μ) | | | | |
| Ave. particle diameter | 1–10 | 1–10 | 5–20 | 0.1–2 |

TABLE IV-4-continued

| | Comparative Example | | | |
|---|---|---|---|---|
| Evaluation | IV-1 | IV-2 | IV-3 | IV-4 |
| Particle size dist. | 0.1–30 | 0.1–30 | 0.1–40 | 0.1–10 |
| 0° C. | ○ | ◎ | ◎ | ◎ |
| Room temp. | ○ | ○ | ◎ | ○ |
| 37° C. | Δ | Δ | Δ | Δ |
| 50° C. | Δ | Δ | Δ | Δ |

Example IV-7: Sunburn Preventing Emulsion

| (1) Purified water | Balance |
|---|---|
| (2) Sodium chloride | 1.0 wt % |
| (3) Sodium glutamate | 1.0 |
| (4) Propylene glycol | 8.0 |
| (5) Pentaerythritol tetra-2-ethylhexanoate | 1.0 |
| (6) Cetyl-2-ethylhexanoate | 1.0 |
| (7) Methylphenylpolysiloxane | 5.0 |
| (8) Decamethylcyclopentasiloxane | 15.0 |
| (9) Torayfil E-505C | 2.5 |
| (10) Aerosil R972 | 1.0 |
| (11) Silicone SC9450N (made by Shinetsu Silicone, HLB = 4.5) | 1.0 |
| (12) Diglycerol monoisostearate (HLB = 5.5) | 1.0 |
| (13) Bentone 38 | 0.1 |
| (14) Octylmethoxycinnamate | 10.0 |
| (15) 2,4-dihydroxybenzophenone | 3.0 |
| (16) Methyl parabene | q.s. |
| (17) Perfume | q.s. |

Method of Production (5), (6), (7), (8), (11), (12), (13), (14), (15), (16) and (18) were mixed at room temperature to produce an oil phase into which the powders of (9) and (10) were gradually added and homogeneously dispersed. Next, (2) and (3) were dissolved in (1) into which was then added (17) dissolved in (4) to obtain an aqueous phase which was then gradually added to the oil phase and homogeneously dispersed by a homomixer, then the emulsion granules were made even to obtain a sunburn preventing emulsion.

As explained above, according to the present invention, it is possible to obtain a water-in-oil emulsion which exhibits an excellent emulsion state, is free from changes due to temperature or the elapse of time, and further has a good spreadability on the skin when applied and has a fresh, refreshing, clean, excellent feeling in use.

We claim:

1. A water-in-oil emulsion cosmetic composition comprising a mixed powder of (A) an organopolysiloxane elastomer spherical powder having an average particle size of 2.0 to 5.0 μm and a particle size distribution of 1 to 15 μm and (B) a hydrophobic silica powder having trimethylsilylated or dimethylsilylated hydroxy groups on the surface thereof and having an average particle size of not more than 2.0 μm, wherein the weight ratio of (A) and (B) is 1:0.1 to 1:5, (C) an oil phase, (D) an emulsifying agent having an HLB value of not more than 7 and (E) water.

2. A water-in-oil emulsion cosmetic composition as claimed in claim 1, wherein the weight ratio of the mixed powder of (A)+(B) to the oil phase (C) is 1:5 to 1:30.

3. A water-in-oil emulsion cosmetic composition as claimed in claim 2, wherein the content of (A)+(B)+(C) is 9.0 to 90.0% by weight, the content of the emulsifying agent having an HLB value of not more than 7 (D) is 0.01 to 5.0% by weight, and the content of the water (E) is 9.0 to 90.0% by weight.

4. A water-in-oil emulsion cosmetic composition comprising a mixed powder of (A) an organopolysiloxane elastomer spherical powder having an average particle size of 2.0 to 5.0 µm and a size distribution of 1 to 15 µm and (B) a hydrophobic particle silica powder having trimethylsilylated or dimethylsilylated hydroxy groups on the surface there of and having an average particle size of not more than 0.2 µm, wherein the weight ratio of (A) to (B) is 1:0.1 to 1:5, (C') an oil phase containing at least 30% by weight, based upon the total oil phase component, of silicone oil, (D) an emulsifying agent having an HLB value of not more than 7, and (E) water.

5. A water-in-oil emulsion cosmetic composition as claimed in claim 4, wherein the weight ratio of the mixed powder of (A)+(B) to the oil phase (C') is 1:5 to 1:30.

6. A water-in-oil emulsion cosmetic composition as claimed in claim 5, wherein the content of (A)+(B)+(C') is 9.0 to 90.0% by weight, the content of the emulsifying agent (D) having an HLB value of not more than 7 is 0.01 to 5.0% by weight, and the content of the water (E) is 9.0 to 90.0% by weight.

7. A water-in-oil emulsion cosmetic composition comprising a mixed powder of (A) an organopolysiloxane elastomer spherical powder having an average particle size of 2.0 to 5.0 µm and a particle size distribution of 1 to 15 µm and (B) a hydrophobic silica powder having trimethylsilylated or dimethylsilylated hydroxy groups on the surface there of and having an average particle size of not more than 0.2 µm, wherein the weight ratio of (A) to (B) is 1:0.1 to 1:5, (C') an oil phase containing at least 30% by weight, based upon the total oil phase component, of silicone oil, (D) an emulsifying agent having an HLB value of not more than 7, (E) water, and (F) a metallic soap.

8. A water-in-oil emulsion cosmetic composition as claimed in claim 7, wherein the weight ratio of the mixed powder of (A)+(B) to the oil phase (C') is 1:5 to 1:30.

9. A water-in-oil emulsion cosmetic composition as claimed in claim 8, wherein the content of (A)+(B)+(C') is 4.0 to 90.0% by weight, the content of the emulsifying agent (D) having an HLB value of not more than 7 is 0.01 to 5.0% by weight, the content of the water (E) is 9.0 to 95.0% by weight and the content of the metallic soap (F) is 0.01 to 5.0% by weight.

10. A water-in-oil emulsion cosmetic composition as claimed in claim 7, wherein the average particle size of the emulsion particles is 1.0 to 10.0 µm and the particle size distribution is 0.1 to 20 µm.

11. A water-in-oil emulsion cosmetic composition comprising a mixed powder of (A) an organopolysiloxane elastomer spherical powder having an average particle size of 2.0 to 5.0 µm and a particle size distribution of 1 to 15 µm and (B) a hydrophobic silica powder having trimethylsilylated or dimethylsilylated hydroxy groups on the surface there of and having an average particle size of not more than 0.2 µm, wherein the weight ratio of (A) to (B) is 1:0.1 to 1:5, (C') an oil phase containing at least 30% by weight, based upon the total oil phase component, of silicone oil, (D) an emulsifying agent having an HLB value of not more than 7, (E) water, and (G) an organically modified clay mineral.

12. A water-in-oil emulsion cosmetic composition as claimed in claim 11, wherein the weight ratio of the mixed powder of (A)+(B) to the oil phase (C') is 1:4 to 1:40.

13. A water-in-oil emulsion cosmetic composition as claimed in claim 12, wherein the content of (A)+(B)+(C') is 4.0 to 90.0% by weight, the content of the emulsifying agent (D) having an HLB value of not more than 7 is 0.01 to 5.0% by weight, the content of the water (E) is 9.0 to 95.0% by weight and the content of the organically modified clay mineral (G) is 0.01 to 5.0% by weight.

14. A water-in-oil emulsion cosmetic composition as claimed in claim 11, wherein the average particle size of the emulsion particles is 1.0 to 20.0 µm and the particle size distribution is 0.1 to 30 µm.

* * * * *